(12) United States Patent
Pardee et al.

(10) Patent No.: US 6,875,745 B2
(45) Date of Patent: Apr. 5, 2005

(54) METHOD AND COMPOSITION FOR THE TREATMENT OF CANCER

(75) Inventors: Arthur B. Pardee, Cambridge, MA (US); Chiang J. Li, West Roxbury, MA (US); Youzhi Li, Dedham, MA (US)

(73) Assignee: Dana Farber Cancer Institute, Inc., Boston, MA (US)

( * ) Notice: Subject to any disclaimer, the term of this patent is extended or adjusted under 35 U.S.C. 154(b) by 0 days.

(21) Appl. No.: 10/683,199

(22) Filed: Oct. 9, 2003

(65) Prior Publication Data

US 2004/0087610 A1 May 6, 2004

Related U.S. Application Data

(63) Continuation of application No. 09/958,479, filed as application No. PCT/US00/10169 on Apr. 14, 2000, now Pat. No. 6,664,288.
(60) Provisional application No. 60/129,261, filed on Apr. 14, 1999.

(51) Int. Cl.[7] .................... A61K 31/70; A61K 31/519; A61K 31/505; A61K 31/35
(52) U.S. Cl. ...................... 514/25; 514/23; 514/33; 514/34; 514/256; 514/262.1; 514/264.1; 514/274; 514/275; 514/454; 514/455; 514/922
(58) Field of Search .................... 514/23, 25, 33, 514/34, 256, 262.1, 264.1, 274, 275, 454, 455, 922, 262, 264

(56) References Cited

U.S. PATENT DOCUMENTS

| | | | | |
|---|---|---|---|---|
| 5,728,687 A | * | 3/1998 | Bissery | ................. 514/90 |
| 5,763,625 A | * | 6/1998 | Boothman et al. | .......... 549/390 |
| 5,919,816 A | * | 7/1999 | Hausheer et al. | ........... 514/449 |
| 6,664,288 B1 | * | 12/2003 | Pardee et al. | ............... 514/449 |

FOREIGN PATENT DOCUMENTS

WO     WO 96/33988     10/1996

OTHER PUBLICATIONS

Coppoc, "Chemotherapy of Neoplastic Diseases", Chapter 58, Purdue Research Foundation (1996).*
Boothman, et al., *Cancer Res.*, 49(3):605–612 (1989).
Katz, et al., *Eur. J. Cancer*, 26(6);724–727 (1990).
Li, et al., *J. Biol. Chem.*, 268(30):22463–22468 (1993).
Li, et al., *PNAS*, 96(23):13369–13374 (1999).
Supplementary European Search Report for EP 00 92 2237, mailing date: May 19, 2004.

\* cited by examiner

*Primary Examiner*—Raymond J. Henley, III
(74) *Attorney, Agent, or Firm*—Mintz, Levin, Cohn, Ferris, Glovsky & Popeo, PC; Ivor R. Elrifi; Matthew Pavao

(57) ABSTRACT

We have discovered that the administration of a G1 and/or S phase drug such as β-lapachone in combination with a G2/M drug such as a taxane derivative such as paclitaxel resulted in a greater than additive (i.e., synergistic) reduction in the number of tumors (and tumor volume) as compared with the administration of these agents alone. In addition, no signs of toxicity or weight loss were observed. The present invention relates to a method for treating a mammalian tumor using combinations such as a taxane derivative, preferably paclitaxel, and a β-lapachone, or a derivative or analog thereof.

14 Claims, 7 Drawing Sheets

METHOD AND COMPOSITION FOR THE TREATMENT OF CANCER

RELATED APPLICATIONS

The present patent application is a continuation of U.S. patent application Ser. No. 09/958,479, filed Feb. 7, 2002, now U.S. Pat. No. 6,664,288, which is a 371 of PCT/US00/10169, filed Apr. 14, 2000, which claims the benefit of U.S. Provisional Application No. 60/129,261, filed Apr. 14, 1999. The contents of these applications are incorporated herein by reference in their entireties.

BACKGROUND OF THE INVENTION

The treatment of cancer has thus far proved problematic. While "cancers" share many characteristics in common, each particular cancer has its own specific characteristics. Genetics and environmental factors have a complex interplay in severity and prognosis of treatment. Thus, treatment must be carefully tailored.

Certain pharmaceutical treatments have proved useful for one form of cancer, but not others (Hollad and Frei, et al, *Cancer Medicine*, 4th ed. Publisher Williams & Wilkens). Other treatments such as radiation, while partially useful for a range of cancers, do not typically result in a complete cure. Indeed, given the severity of many cancers and the mortality rate, a drug can be deemed successful if it improves quality of life, e.g., by delaying growth of tumors, or prolongs life—without actually curing the condition. Thus, in many circumstances, an individual is treated with a compound or combination of treatments that can eliminate 90–95% of the malignant cells, but the remaining cells can regrow and metastasize, ultimately resulting in death. Among cancers with particularly poor ultimate prognoses is ovarian cancer.

Combination therapies, while desirable, are a hit or miss proposition. The treatments are typically not additive. In many cases, cross effects and treatment load can result in lower effectiveness for the combinations, than either treatment alone. Problems encountered include multiple drug resistance (MDR), where the malignant cell in essence pumps the cytotoxic compounds and other compounds out of the cell, thereby preventing continued useful treatment of the cancer.

There are a number of cytotoxic agents that are currently being used or studied for the treatment of cancer. One of these, Paclitaxel, (also referred to as TAXOL®) was first identified in 1971 by Wani and collaborators (Wani M C et al., 1971 *J. Am. Chem. Soc.*, 93: 2325–2327) following a screening program of plant extracts of the National Cancer Institute. This complex diterpene shows cytotoxic activity against several types of tumors and is presently used in the treatment of some cancers such as ovarian and breast cancers. Clinical studies suggest that TAXOL® could eventually be used in the treatment of over 70% of human cancers.

Paclitaxel differs from other cytotoxic drugs by its unique mechanism of action. It interferes with cell division by manipulating the molecular regulation of the cell cycle. Paclitaxel binds to tubulin, the major structural component of microtubules that are present in all eukaryotic cells. Unlike other antimitotic agents such as vinca alkaloids and colcichine, which inhibit the polymerization of tubulin, paclitaxel promotes this assembly of tubulin and stabilizes the resulting microtubules. This event leads to the interruption of cell division, and ultimately to cell death.

The antitumor property of taxoid compounds has also lead to the generation of new anticancer drugs derived from taxanes. Taxotere™ (sold by Rhône-Poulenc Rorer), which is produced from 10-deacetylbaccatin III by hemisynthesis, is currently used in the treatment of ovarian and breast cancers.

While agents such as TAXOL® and Taxotere have made an advance in the treatment of metastatic ovarian and metastatic breast cancer, the majority of those treated still ultimately succumb to these diseases.

β-lapachone, a quinone, is derived from lapachol (a naphthoquinone) which can be isolated from the lapacho tree (*Tabebuia avellanedae*), a member of the catalpa family (Bignoniaceae). Like camptothecin and topotecan, β-lapachone inhibits DNA Topoisomerase I (Li, C. J., et al., J. Biol. Chem., 1993). This compound has been found to be effective against several types of cancer cells in vitro, including lung, breast, colon and prostate cancers and malignant melanoma (Li, C. J., et al., *Cancer Research* 55:3712–3715 (1995) and unpublished data).

β-lapachone works by disrupting DNA replication. Topoisomerase I is an enzyme that unwinds the DNA that makes up the chromosomes. The chromosomes must be unwound in order for the cell to use the genetic information to synthesize proteins; β-lapachone keeps the chromosomes wound tight, and so the cell can't make proteins. As a result, the cell stops growing. Because cancer cells are constantly replicating and circumvent many mechanisms that restrict replication, as is the case with normal cells, they are more vulnerable to topoisomerase inhibition than are normal cells. However, treatment with these compounds is also only partially successful—inhibiting and delaying growth of the malignant cells.

No single drug or drug combination is curative for advanced metastatic cancer and patients typically succumb to the cancers in several years. Thus, new drugs or combinations that can prolong onset of life-threatening tumors and/or improve quality of life by further reducing tumor-load are very important.

SUMMARY OF THE INVENTION

We have surprisingly discovered that the administration of a compound that targets cells at G1 and/or S phase such as a topoisomerase I inhibitor such as β-lapachone in combination with a compound that targets such cells at G2/M phase, e.g., a taxane derivative such as paclitaxel resulted in an unexpectedly greater than additive (i.e., synergistic) reduction in the number of tumors (and tumor volume in a mammal with metastatic tumors) as compared with the administration of these agents alone. Furthermore, the tumors did not grow back in several months of observation. In addition, no signs of toxicity or weight loss were observed in mammals so treated.

Accordingly, the present invention relates to a method for treating a mammalian tumor using a combination of a G2/M phase drug including, but not limited to, taxane, its derivatives and analogs, more preferably paclitaxel, and a G1 and/or S phase drug, preferably β-lapachone, or a derivative or analog thereof.

A list of two representative compounds is described in Table 1, infra. The combination of the present invention is particularly advantageous in the treatment of patients who have chemotherapeutically refractive metastatic cancer. The method of the present invention comprises administering to the mammal in combination an effective amount of a G1 and S phase drug, a G1 phase drug, a S phase drug, in combination with a G2/M drug. Preferably, the combination is (1) a topoisomerase I inhibitor such as β-lapachone or its derivatives or analog thereof; and (2) taxane, its derivatives or analogs and pharmaceutically acceptable salts thereof.

As used herein, the phrase "taxane derivative" means any taxane which is or may be used in cancer chemotherapy due to its antineoplastic properties. TAXOL® is a preferred taxane derivative.

As further used herein, the phrase "β-lapachone" means lapachone (3,4-dihydro-s, 3-dimethyl-2H-naphthol[1,3-b]

pyran-5,6-clone) and derivatives and analogs thereof Preferred derivatives and analogs are discussed below.

BRIEF DESCRIPTION OF THE DRAWINGS

FIG. 7A is the control. FIG. 7B is the combination.

DETAILED DESCRIPTION

Figure 1A:
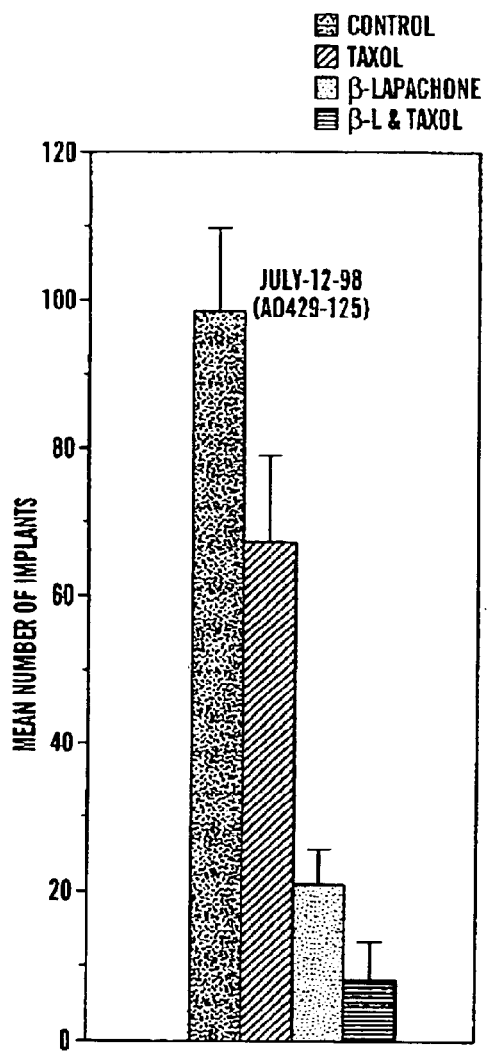
FIGS. 1A and 1B illustrate the results of Experiment 1.

This invention provides for advantageous combination therapies for cancers, including, but not limited to, breast, ovarian and prostate cancer using methods which employ administration of a G1 and/or S phase compound with a G2/M phase compound.

In one embodiment, the invention is directed to a method for treating a subject having malignant cells or inhibiting further growth of such malignant cells by using a compound that targets such cells at G1 and/or S phase checkpoints, simultaneously with/or followed by using a drug that acts at G2/M checkpoints. Individual compounds satisfying this criteria are known to those of ordinary skill in the art. For example, β-lapachone and its derivatives are G1 and S phase drugs. Whereas taxol and its derivatives are G2/M drugs. A list of representative compounds is set forth below in Table 1:

TABLE 1

| Type | Category | | Compound Name | Chemical Formula |
|---|---|---|---|---|
| 1. | G1 and S phase drug | | β-lapachone Reduced β-lapachone | |
| 2. | G1 phase drugs | | Lovastatin | [1S[1α(R*),3α7β,8β S*,4S*),8αβ]]-Methylbutanoic acid 1,2,3,7,8,8a-hexahydro-3,7-dimethyl-8-[2-(tetrahydro-4-hydroxy-6-oxo-2H-pyran-2-yl)ethyl]-1-naphthalenyl ester |
| | | | Mimosine | α-Amino-3-hydroxy-4-oxo-1(4H)-pyridine propanoic acid |
| | | | Tamoxifen | [Z]-2-[4-(1,2-Diphenyl-1-butenyl)-phenoxy]-N,N-dimethylethanamine |
| 3. | S phase drugs | | Gemcitabine | 2',2'difluorodeoxycytidine |
| | | | 5-FU | 5-fluorouracil |
| | | | MTX | Methotrexate; N-[4-[[(2,4-Diamino-6-pteridinyl)methyl]methylamino] benzoyl]-L-glutamic acid |
| 4. | G2/M drugs | | | |
| | | (i) Microtubule-targeting | Taxol | 5-beta,20-epoxy-1,2-alpha,4,7-beta,10-beta,13-alpha-hexahydroxy-tax-11-en-9-one 4,10-diacetate 2-benzoate 13-ester with (2R,3S)-N-benzoyl-3-phenyl-isoserine |
| | | | Docetaxel | N-debenzoyl-N-tert-butoxycarbonyl-10-deacetyl taxol |
| | | | Epothilone | Epithilone Polyketides A, B, C or D (desoxy-epothilone) |
| | | | Vincristin | 22-Oxovincaleukoblastine |
| | | | Vinblastin | Vincaleukoblastine |
| | | | Nocodazole | 2-Benzimidazolecarbamic acid, 5-(2-thenoyl)-, methyl ester |
| | | | Navelbine | Vinorelbine |
| | | (ii) Topoisomerase Poisons | Teniposide | VM-26; [5R-5α,5αβ,8αα,9β (R*)]]-5,8,8a,9-tetrahydro-5-(4-hydroxy-3,5-dimethoxyphenyl)-9-[[4,6-O-(2-thienylmethylene)-β-D-glucopyranosyl]oxy]furo[3',4':6,7]naphtho[2,3-d]-1,3-dioxol-6(5aH)-one |

TABLE 1-continued

| Type | Category | Compound Name | Chemical Formula |
|---|---|---|---|
| | | Etoposide | VP-16; 4'-Demethylepipodophyllotoxin ethylidene-B-D-glucoside |
| | | Adriamycin | Doxorubicin; 14-Hydroxydaunomycin |
| | | Camptothecin | Cerubidin; Leukaemomycin C; |
| | | Daunorubicin | Rubidomycin; Rubomycin C |
| | | Dactinomycin | Actactinomycin A IV; Actinomycin C1; Actinomycin-[threo-val-pro-sar-meval] |
| | | Mitoxantrone | Idamycin; 4-demethoxy-daunorubicin |
| | | Amsacrine | |
| | | Epirubicin | |
| | | Idarubicin | |

The combinations of the present invention are particularly advantageous as shown by the example with β-lapachone and taxol where synergistic results were obtained. Molecular changes underlying cell cycle delay at multiple checkpoints, for example G1 and/or S phase and G2/M phase, can for example result in the synergistic induction of apoptosis in malignant cells. Although not wishing to be bound by theory, it is believed that the synergistic effect is mediated by inhibition of cdc2 kinases and upregulation of p21. p21 controls G1 and S phase checkpoints (Elledge, S. J. (1996) Science 274, 1664–1672), and is involved in the regulation of the G2/M checkpoint (Iartwell L. H. et al., M. B. (1994) Science, 266, 1821–1828). Cell cycle checkpoints are also regulated by cdc2 kinases and their inhibitors (Elledge, S. J. (1996) Science 274, 1664–1672 and Nurse, P. (1997) Cell 91, 865–867).

Preferably, the G1 and/or S phase compounds are administered prior to, or simultaneously with compounds that target a cell at the G2/M phase checkpoint. More preferably, the compounds are administered prior to the compounds that target a cell at the G2/M checkpoint.

Preferred G1 and/or S phase checkpoint targeting compounds include G1 and/or S phase drugs (for example, β-lapachone), G1 phase drugs (for example, lovastatin, mimosine, tamoxifen, etc.) and S phase drugs (for example, gemcitabine, 5-FU, MIX, etc.). β-lapachone, its derivatives and analogs are more preferred.

Further, G1 and/or S phase checkpoint targeting drugs include derivatives of reduced β-lapachone. Reduction of β-lapachone has been shown to be an essential component of β-lapachone activity (see J. J. Pink et al (2000) J Biol. Chem. 275: 5416–5424). Preferably, G1 and/or S phase checkpoint targeting drugs would further include reduced β-lapachone, i.e reduced β-lapachone derivatives or analogs and/or a combination of β-lapachone derivatives or analogs (quinine form) with reduced β-lapachone derivatives or analogs (hydroquinone form). Most preferably, the reduced β-lapachone, its derivatives or analogs would include modified hydroquinone groups in the reduced β-lapachone as shown in Formula Ia where the R' and/or R" group(s) are converted to, for example, succinates, amino acids etc.

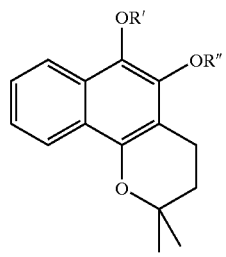

Formula Ia

Preferred G2/M phase checkpoint targeting compounds include microtuble-targeting drugs (for example, taxol, docetaxel, vincristin, vinblastin, nocodazole, epothilones, navelbine, etc.) and topoisomerase poisons (for example, teniposide, etoposide, adriamycin, camptothecin, daunorubicin, dactinomycin, mitoxantrine, amsacrine, epirubicin, idarubicin, etc.).

Epothilones (epothilone polyketides) are microtubule targeting drugs which stabilize microtubules by means of the same mechanisms as taxol (see Litang, et al. (2000) Science 287, 640–642). The epothilones are advantageous as they are effective against taxol-resistant tumors and are sufficiently water soluble. Epothilones A and B are the most abundant in nature and 12,13-desoxy-epothilone B (epothilone D) has the highest therapeutic index. Epothilones (A, B, C, D or mixtures thereof) can be used in combination with β-lapachone and this could in a synergistic induction of apoptosis in malignant cells which is similar to the combination of β-lapachone and taxol, as described earlier. For the purpose of this invention, epothilone would refer to epothilones A, B, C or D (desoxy-epothilone).

Preferred combinations include:
β-lapachone with taxol; β-lapachone with docetaxel; β-lapachone with vincristin; β-lapachone with vinblastin; β-lapachone with nocodazole; β-lapachone with teniposide; β-lapachone with etoposide; β-lapachone with adriamycin; β-lapachone with epothilone; β-lapachone with navelbine; β-lapachone with camptothecin; β-lapachone with daunorubicin; β-lapachone with dactinomycin; β-lapachone with mitoxantrone; β-lapachone with amsacrine; β-lapachone with epirubicin; or β-lapachone with idarubicin.

Reduced β-lapachone with taxol; reduced β-lapachone with docetaxel; reduced β-lapachone with vincristin; reduced β-lapachone with vinblastin; reduced β-lapachone with nocodazole; reduced β-lapachone with teniposide; reduced β-lapachone with etoposide; reduced β-lapachone with adriamycin; reduced β-lapachone with epothilone; reduced β-lapachone with navelbine; reduced β-lapachone with camptothecin; reduced β-lapachone with daunorubicin; reduced β-lapachone with dactinomycin; reduced β-lapachone with mitoxantrone; reduced β-lapachone with amsacrine; reduced β-lapachone with epirubicin; or reduced β-lapachone with idarubicin.

Lovastatin with taxol; lovastatin with docetaxel; lovastatin with vincristin; lovastatin with vinblastin; lovastatin with nocodazole; lovastatin with teniposide; lovastatin with etoposide; lovastatin with adriamycin; lovastatin with epothilone; lovastatin with navelbine; lovastatin with camptothecin; lovastatin with daunorubicin; lovastatin with dactinomycin; lovastatin with mitoxantrone; lovastatin with amsacrine; lovastatin with epirubicin; or lovastatin with idarubicin.

Mimosine with taxol; mimosine with docetaxel; mimosine with vincristin; mimosine with vinblastin; mimosine with nocodazole; mimosine with teniposide; mimosine with etoposide; mimosine with adriamycin; mimosine with epothilone; mimosine with navelbine; mimosine with camptothecin; mimosine with daunorubicin; mimosine with dactinomycin; mimosine with mitoxantrone; mimosine with amsacrine; mimosine with epirubicin; or mimosine with idarubicin.

Tamoxifen with taxol; tamoxifen with docetaxel; tamoxifen with vincristin; tamoxifen with vinblastin; tamoxifen with nocodazole; tamoxifen with teniposide; tamoxifen with etoposide; tamoxifen with adriamycin; tamoxifen with epothilone; tamoxifen with navelbine; tamoxifen with camptothecin; tamoxifen with daunorubicin; tamoxifen with dactinomycin; tamoxifen with mitoxantrone; tamoxifen with amsacrine; tamoxifen with epirubicin; or tamoxifen with idarubicin.

Gemcitabine with taxol; gemcitabine with docetaxel; gemcitabine with vincristin; gemcitabine with vinblastin; gemcitabine with nocodazole; gemcitabine with teniposide; gemcitabine with etoposide; gemcitabine with adriamycin; gemcitabine with epothilone; gemcitabine with navelbine; gemcitabine with camptothecin; gemcitabine with daunorubicin; gemcitabine with dactinomycin; gemcitabine with mitoxantrone; gemcitabine with amsacrine; gemcitabine with epirubicin; or gemcitabine with idarubicin.

5-FU with taxol; 5-FU with docetaxel; 5-FU with vincristin; 5-FU with vinblastin; 5-FU with nocodazole; 5-FU with teniposide; 5-FU with etoposide; 5-FU with adriamycin; 5-FU with epothilone; 5-FU with navelbine; 5-FU with camptothecin; 5-FU with daunorubicin; 5-FU with dactinomycin; 5-FU with mitoxantrone; 5-FU with amsacrine; 5-FU with epirubicin; or 5-FU with idarubicin.

MTX with taxol; MTX with docetaxel; MTX with vincristin; MTX with vinblastin; MTX with nocodazole; MTX with teniposide; MTX with etoposide; MIX with adriamycin; MTX with epothilone; MTX with navelbine; MTX with camptothecin; MTX with daunorubicin; MTX with dactinomycin; MTX with mitoxantrone; MTX with amsacrine; MTX with epirubicin; or MTX with idarubicin.

The combination of the present invention results in a surprising synergy which is beneficial in reducing tumor burden load and/or regressing tumor growth, especially in patients with metastatic disease.

Preferably, the cancers treated are breast, ovarian, prostate, lung, colon and melanoma. More preferably, the cancer is ovarian.

The compounds can be administered by any means known in the art. Such modes include oral, rectal, nasal, topical (including buccal and sublingual) or parenteral (including subcutaneous, intramuscular, intravenous and intradermal) administration.

For ease to the patient oral administration is preferred. However, typically oral administration requires a higher dose than an intravenous administration. Thus, depending upon the situation—the skilled artisan must determine which form of administration is best in a particular case—balancing dose needed versus the number of times per month administration is necessary.

In administering the compounds one can use the normal dose of each compound individually. However, preferably one uses a lower level—typically 75% or less of the individual amount, more preferably 50% or less, still more preferably 40% or less.

The individual components will be addressed in more detail below.

One preferred component of the combination therapy described is a taxane derivative. The taxanes are a family of terpenes, including, but not limited to paclitaxel and docetaxel (Taxatere), which were derived primarily from the Pacific yew tree. *Taxus brevifoila*, and which have activity against certain tumors, particularly breast and ovarian tumors. Paclitaxel is a preferred taxane. It is considered an antimicrotubule agent that promotes the assembly of microtubules from tubulin dimers and stabilizes microtubules by preventing depolymerization. This stability results in the inhibition of the normal dynamic reorganization of the microtubule network that is essential for vital interphase and mitotic cellular functions. The term "paclitaxel" includes both naturally derived and related forms and chemically synthesized compounds or derivatives thereof with antineoplastic properties including deoxygenated paclitaxel compounds such as those described in U.S. Pat. No. 5,440,056, herein incorporated by reference, and that sold is sold as TAXOL® by Bristol-Myers Oncology. Chemical formulas for paclitaxel are known and disclosed in U.S. Pat. No. 5,440,056. In addition to TAXOL®, other derivatives are well known, e.g., those mentioned in "Synthesis and Anticancer Activity of TAXOL® other Derivatives," D. G. I. Kingston et al., Studies in Organic Chemistry, vol. 26, entitled "New Trends in Natural Products Chemistry" (1986), Atta-ur-Rahman, P. W. le Queene, Eds. (Elvesier, Amsterdam 1986), pp. 219–235. Still other taxane derivatives are known in the art and include those, for example, disclosed in U.S. Pat. Nos. 5,773,461; 5,760,072; 5,807,888; and 5,854,278.

The G2/M compound such as the taxane derivative may be administered in any manner found appropriate by a clinician in generally accepted efficacious dose ranges such as those described in the *Physician Desk Reference*, 53th Ed. (1999), Publisher Edward R. Barnhart, New Jersey ("PDR") for paclitaxel.

In general, the G2/M compound such as the taxane derivative is administered intravenously at dosages from about 135 to about 300 mg/m$^2$, preferably from about 135 to about 175 mg/m$^2$, and most preferably about 175 mg/m$^2$. It is preferred that dosages be administered over a time period of about 1 to about 24 hours, typically over a period of about 3 hours. Dosages can be repeated from 1 to about 4 weeks or more, preferably from about 2 to about 3 weeks.

The drug may be administered in any form such as by injection or oral forms. Liposome formulations, for example, have been described See, e.g. U.S. Pat. No. 5,424,073, which is herein incorporated by reference.

As previously mentioned, the G2/M drug such as taxane derivative, preferably paclitaxel, will be administered in a similar regimen with a G1 and/or S phase drug such as β-lapachone or a derivative thereof, although the amounts will preferably be reduced from that normally given. It is preferred that for example the taxane be administered at the same time as for example the β-lapachone or after the β-lapachone has been given to the patient, typically about 24 hours after the β-lapachone has been administered.

The other component of the combination therapy described is β-lapachone or a derivative or analog thereof.

β-lapachone (3,4-dihydro-s,3-dimethyl-2H-naphthol[1,3-b]pyran-5,6-clone) is a simple plant product with a chemical structure different from currently used anti-cancer drugs. It is obtained by sulfuric acid treatment of the naturally occurring lapachol, which is readily isolated from *Tabebuia avellanedae* growing mainly in Brazil, or is easily synthesized from lomatiol, isolated from seeds of lomatia growing in Australia (Hooker, S., et al., *J. Am. Chem. Soc.*, 58:1181–1190 (1936); Goncalves de Lima, O., et al., *Rev. Inst. Antibiot. Univ. Recife.*, 4:3–17 (1962)).

β-lapachone has been shown to have a variety of pharmacological effects. β-lapachone is a topoisomerase I inhibitor but acts by a different mechanism than camptothecin (Li, C. J., et al., *J. Biol. Chem.*, 268:22463–22468 (1993). Numerous β-lapachone derivatives have been synthesized and tested as anti-viral and anti-parasitic agent (Goncalves, A. M., et al., *Mol. Biochem. Parasitology*, 1:167–176 (1980); Schaffner-Sabba, K., et al., *J. Med. Chem.*, 27:990–994 (1984); Li, C., et al., *Proc. Natl. Acad. Sci. USA*, 90: 1842 (1993)). β-lapachone and its derivatives, e.g. 3-allyl-β-lapachone, show anti-trypanosomal effects (Goncalves, A. M., et al., supra), the mechanism of which is unclear. β-lapachone has also been shown to be a DNA repair inhibitor which sensitizes cells to DNA damaging agents (Boorstein, R. J., et al., *Biochem. Biophys. Res. Commun.*, 118:828–834, (1984); Boothman, D. A, et al., *J. Cancer Res.*, 49:605–612 (1989)). β-lapachone is well tolerated in dogs, rats, mice, and chickens. The maximum tolerated dose, when given p.o. daily for one month, is 200 mg/kg in rats, and 100 mg/kg in dogs. Higher doses cause gastric ulceration and loss of erythrocytes, but not signs of bone marrow suppression (Ciba-Geigy, personal communication).

β-lapachone derivatives and analogs are known in its art and are disclosed, for example, in U.S. Pat. No. 5,828,700; WO97/08162; and U.S. Pat. No. 5,703,625. Preferred derivatives and analogs include compounds of the following formulae I and II.

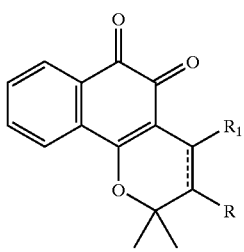

Formula I

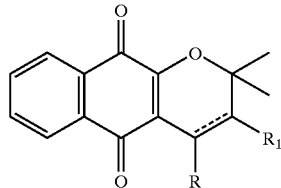

Formula II wherein R and $R_1$ are each independently selected from the group consisting of hydrogen, hydroxy, thio (SH), halogen (e.g. fluoro, chloro and bromo), substituted and unsubstituted aryl, substituted and unsubstituted alkenyl substituted and unsubstituted alkyl and substituted and unsubstituted alkoxy, and salts thereof, wherein the dotted double bond between the ring carbons to which R and $R_1$ are bonded represent an optional ring double bond. The alkyl groups preferably have from 1 to about 15 carbon atoms, more preferably from 1 to about 10 carbon atoms, still more preferably from 1 to about 6 carbon atoms. As used herein, the term alkyl unless otherwise modified refers to both cyclic and noncyclic groups, although of course cyclic groups will comprise at least three carbon ring members. Straight or branched chain noncyclic alkyl groups are generally more preferred than cyclic groups. Straight chain alkyl groups are generally more preferred than branched. The alkenyl groups preferably have from 2 to 15 carbon atoms, more preferably from 2 to about 10 carbon atoms, still more preferably from 2 to about 6 carbon atoms. Especially preferred alkenyl groups have 3 carbon atoms (i.e., 1-propenyl or 2-propenyl), with the allyl moiety being particularly preferred. Phenyl and naphthyl are generally preferred aryl groups. Alkoxy groups include those alkoxy groups having one or more oxygen linkage and preferably have from 1 to 15 carbon atoms, more preferably from 1 to about 6 carbon atoms. Said substituted R and $R_1$ groups may be substituted at one or more available positions by one or more suitable groups such as, for example, alkyl groups such as alkyl groups having from 1 to 10 carbon atoms or from 1 to 6 carbon atoms, alkenyl groups such as alkenyl groups having from 2 to 10 carbon atoms or 2 to 6 carbon atoms, aryl groups having from 6 to 10 carbon atoms, halogen such as fluoro, chloro and bromo, and N, O and S, including heteroalkyl, e.g., heteroalkyl having one or more of said hetero atom linkages (and thus including alkoxy, aminoalkyl and thioalkyl) and from 1 to 10 carbon atoms or from 1 to 6 carbon atoms.

Compounds of formulae I and II can readily be made or obtained. (See Pardee, A, et al., *Cancer Research*, 49, 1–8 (1989); Schaffner-Sabba, K, et al., *Journal of Medicinal Chemistry*, 27, no. 8 990–994 (1984); S. Hooker, 58, 1181–1197 (1936).

Preferred compounds of formula I include β-lapachone, 3-allyl-β-lapachone, 3-bromo-β-lapachone and 3-OH-β-lapachone. 3-allyl-β-lapachone and 3-bromo-β-lapachone are more preferred.

Preferred compounds of formula II include 3-bromo-alpha-lapachone.

β-lapachone analogs of formula III, set forth below, can also be used in the compositions and methods of the present invention.

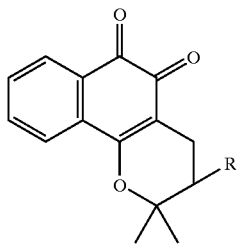

Formula III where R is $(CH_2)_n-R_1$
where n is an integer from 0–10 and $R_1$ is hydrogen, an alkyl, an aryl, a heteroaromatic, a heterocyclic, an aliphatic, an alkoxy, a hydroxy, an amine, a thiol, an amide, or a halogen side group.

Preferred analogs of formula III include, 3-ethoxycarbonylmethyl-β-lapachone, 3-(2'-Hydroxyethyl)-β-lapachone 3-methyl-β-lapachone, 3-(2'-aminoethyl)-β-lapachone, 3-methoxy-β-lapachone, 3-benzyloxy-β-lapachone, 3-ethoxycarbonylmethoxy-β-lapachone and 3-allyloxy-β-lapachone.

Analogs of formula III can be produced by the methods disclosed in U.S. Pat. No. 5,763,625.

β-lapachone derivatives of formulae IV and V, set forth below, can further be used in the compositions and methods of the present invention.

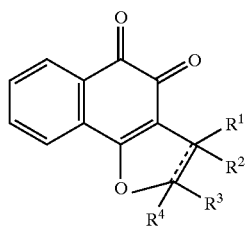

Formula IV

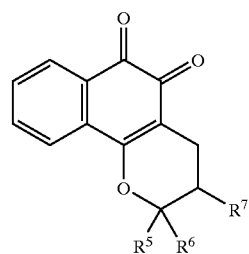

Formula V wherein $R^1-R^6$ are each, independently, selected from the group consisting of H, $C_1-C_6$ alkyl, $C_1-C_6$ alkenyl, $C_1-C_6$ alkoxy, $C_1-C_6$ alkoxycarbonyl, $-(CH_2)_n$-aryl, $(CH_2)_n$-heteroaryl, $-(CH_2)_n$-heterocycle, and $-(CH_2)_n$-phenyl; or $R^1$ and $R^2$ combined are a single substituent selected from the above group, and $R^3$ and $R^4$ combined are a single substituent selected from the above group, in which case—is a double bond; and $R^7$ is H, OH, $C_1-C_6$ alkyl, $C_1-C_6$ alkenyl, $C_1-C_6$ alkoxy, $C_1-C_6$ alkoxycarbonyl, $-(CH_2)_n$-amino, $-(CH_2)_n$-aryl, $-(CH_2)_n$-heteroaryl, $-(CH_2)_n$-heterocycle, or $-(CH_2)_n$-phenyl, wherein n is an integer from 0 to 10.

Preferred analogs of formulae IV and V include 3-(β-alanyl)-β-lapachone and 3-malonyl-β-lapachone.

Analogs of formulae IV and V can be produced by the methods disclosed in U.S. Pat. No. 5,824,700.

Under the combination therapies described here, β-lapachone or a derivative or analog thereof is administered to a patient in at least one dose in the range of 10 to 500,000 µg per kilogram body weight of recipient per day, more preferably in the range of 1000 to 50,000 µg per kilogram body weight per day, most preferably in the range of 5000 to 25,000 µg per kilogram body weight per day. The desired dose is suitably administered once or several more sub-doses administered at appropriate intervals throughout the day, or other appropriate schedule. These sub-doses may be administered as unit dosage forms, for example, containing 1 to 20,000 µg, preferably 10 to 10,000 µg per unit dosage form.

As with the use of other chemotherapeutic drugs, the individual patient will be monitored in a manner deemed appropriate by the treating physician. Typically, no additional drug treatments will occur until, for example, the patient's neutrophil count is at least 1500 cells/mm³. Dosages can also be reduced if severe neutropenia or severe peripheral neuropathy occurs, or if a grade 2 or higher level of mucositis is observed, using the Common Toxicity Criteria of the National Cancer Institute.

The combination therapy agents described here may be administered singly or in a cocktail containing both agents or one of the agents with other therapeutic agents, including but not limited to, immunosuppressive agents, potentiators and side-effect relieving agents. As aforesaid, the therapeutic combination, if administered sequentially, is more effective when the β-lapachone component is administered prior to the taxane derivative. The therapeutic agents will preferably be administered intravenously or otherwise systemically by injection intramuscularly, subcutaneously, intrathecally or intraperitoneally.

The pharmaceutical compositions of this invention which are found in combination may be in the dosage form of solid, semi-solid, or liquid such as, e.g., suspensions, aerosols or the like. Preferably the compositions are administered in unit dosage forms suitable for single administration of precise dosage amounts. The compositions may also include, depending on the formulation desired, pharmaceutically-acceptable, nontoxic carriers or diluents, which are defined as vehicles commonly used to formulate pharmaceutical compositions for animal or human administration. The diluent is selected so as not to affect the biological activity of the combination. Examples of such diluents are distilled water, physiological saline, Ringer's solution, dextrose solution, and Hank's solution. In addition, the pharmaceutical composition or formulation may also include other carriers, adjuvants, or nontoxic, nontherapeutic, nonimmunogenic stabilizers and the like. Effective amounts of such diluent or carrier will be those amounts which are effective to obtain a pharmaceutically acceptable formulation in terms of solubility of components, or biological activity, and the like.

For the purposes of the present invention, the G1 and/or S phase compounds, derivatives or analogs and G2/M compounds, derivatives or analogs described herein include their pharmacologically acceptable salts, preferably sodium; analogs containing halogen substitutions, preferably chlorine or fluorine; analogs containing ammonium or substituted ammonium salts, preferably secondary or tertiary ammonium salts; analogs containing alkyl, alkenyl, aryl or their alkyl, alkenyl, aryl, halo, alkoxy, alkenyloxy substituted derivatives, preferably methyl, methoxy, ethoxy, or phenylacetate; and natural analogs such as naphthyl acetate. Further, the G and/or S phase compounds, derivatives or analogs and G2/M compounds, derivatives or analogs described herein may be conjugated to a water soluble polymers or may be derivatized with water soluble chelating agents or radionuclides. Examples of water soluble polymers are, but not limited to: polyglutamic acid polymer, copolymers with polycaprolactone, polyglycolic acid, polyactic acid, polyacrylic acid, poly (2-hydroxyethyl 1-glutamine), carboxymethyl dextran, hyaluronic acid, human serum albumin, polyalginic acid or a combination thereof Examples of water soluble chelating agents are, but not limited to: DTPA (diethylenetriaminepentaacetic acid), EDTA, DTTP, DOTA or their water soluble salts etc. Examples of radionuclides are, but not limited to: $^{111}$In, $^{90}$Y, $^{166}$Ho, $^{68}$Ga, $^{99m}$Tc, etc.

In therapeutic applications, the dosages of the agents used in accordance with the invention vary depending on the agent, the age, weight, and clinical condition of the recipient patient, and the experience and judgment of the clinician or practitioner administering the therapy, among other factors affecting the selected dosage. Generally, the dose should be sufficient to result in slowing, and preferably regressing, the growth of the tumors and also preferably causing complete regression of the cancer. An effective amount of a pharmaceutical agent is that which provides an objectively identifiable improvement as noted by the clinician or other qualified observer. Regression of a tumor in a patient is typically measured with reference to the diameter of a tumor. Decrease in the diameter of a tumor indicates regression. Regression is also indicated by failure of tumors to reoccur after treatment has stopped.

This invention further includes pharmaceutical combinations comprising a taxane derivative and a dose of β-lapachone or a derivative or analog thereof as provided above and kits for the treatment of cancer patients comprising a vial of the taxane derivative and a vial of β-lapachone or a derivative or analog thereof at the doses provided above. Preferably, the kit contains instructions describing their use in combination.

The documents mentioned herein are incorporated herein by reference.

It is understood that the foregoing detailed description and the following examples are illustrative only and are not to be taken as limitations upon the scope of the invention. Various changes and modifications to the disclosed embodiments, which will be apparent to those skilled in the art, may be made without departing from the spirit and scope of the present invention. Further, all patents, patent applications and publications cited herein are incorporated herein by reference.

EXAMPLES

In Vivo Testing

Experiment 1

Brief description of the tumor model (Cannistra model, Cannistra, et al., *Cancer Res.*, 57:1228–1232 (1997)— Ovary cancer is a highly lethal disease. Metastases occurs predominantly by widespread implantation throughout the abdominal cavity. To test the efficacy of β-lapachone alone and in combination with TAXOL®, we used human ovary cancer cells (36M2) that were originally derived from a patient with malignant ascites. Inoculation of these cells into female nude mice recapitulates the metastatic process as observed in patients. This is a highly metastatic and malignant cancer cell model. In general, tumor nodules on peritoneum and malignant ascites develop 4 to 5 weeks after an inoculation of 10×10$^6$ cells. Metastatic foci can be seen from one week after inoculation.

Animals—Athymic female nude (nu/nu) were used throughout the experiments.

Drugs—β-Lapachone was formulated into solution by using lipidol, a medium agent used clinically. Our success with this formulating agent (lipidol) solved the long-standing problem of insolubility of β-lapachone.

Alternatively, we also find that β-lapachone can be formulated in cremphor plus ethanol [2 (cremphor):1 (ethanol)]. A solution of 20 mg/ml can be prepared at room temperature.

TAXOL® (Ciba-Geigy) formulated solution (patient use standard) was purchased from pharmacy and diluted with Lipidol (Sumitome Pharmaceuticals, Osaka) for the mouse experiment.

Both β-lapachone and TAXOL® solution can be administered either intraperitoneally or intravenously. Intraperitoneally routes for both drugs were used. Lipidol formulation of β-lapachone was used.

Design of Animal Trials

Six mice per group.

Group 1, treated with control vehicle (as in group 4);

Group 2, treated with β-lapachone at 50 mg/kg;

Group 3, treated with TAXOL® at 0.1 mg/kg

Group 4, β-lapachone at 50 mg/kg first, followed by TAXOL® at 0.1 mg/kg the next day. Repeat the cycle after two days.

All treatments were started a week after tumor inoculation. Mice were treated for 10 cycles in total, and were sacrificed for tumor nodule counting two weeks (on day 50) after discontinuation of drug treatment.

Upon sacrifice, antitumor activity in each group was evaluated by counting the number of tumor nodules in the peritoneal cavity, measuring the diameter of the tumors, measuring the volume of the ascites and qualitatively observing the color of the peritoneal wall as an indication of the degree of tumor-induced vascularization.

Toxicity was evaluated by qualitative observation of the general appearance and behavior of the mice prior to sacrifice and by measuring their body weight at various intervals during the course of the treatments.

Figure 1B:
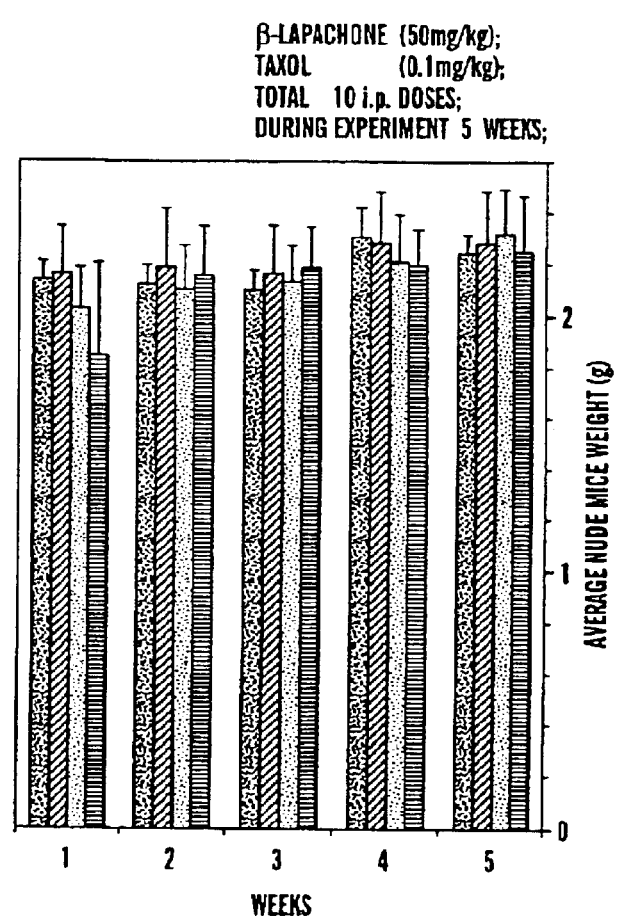

The results of this experiment are set forth in FIGS. 1A and 1B. As can be seen, the combination of β-lapachone and TAXOL® dramatically reduced the number of tumor implants compared to the untreated control group and the groups treated with each agent alone. No toxicity was observed.

Experiment 2

Tumor models and drug formulation were identical to Experiment 1. Again, 6 mice were used for each group. The experimental design has the following modifications: 1) TAXOL® dose were increased by 10 fold; 2) mice were observed for four weeks after the cessation of the drug treatment.

Group 1, treated with control vehicle (as in group 4);

Group 2, treated with β-lapachone at 50 mg/kg;

Group 3, treated with TAXOL® at 1 mg/kg

Group 4, β-lapachone at 50 mg/kg first, followed by TAXOL® 1 mg/kg the next day. Cycle repeated after two days.

Figure 2A:
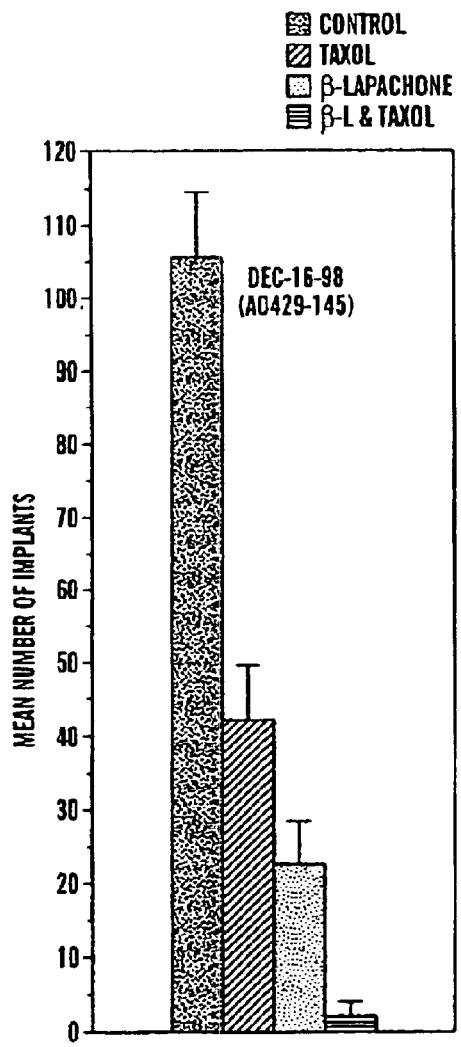
FIGS. 2A and 2B illustrate the results of Experiment 2.
Figure 2B:
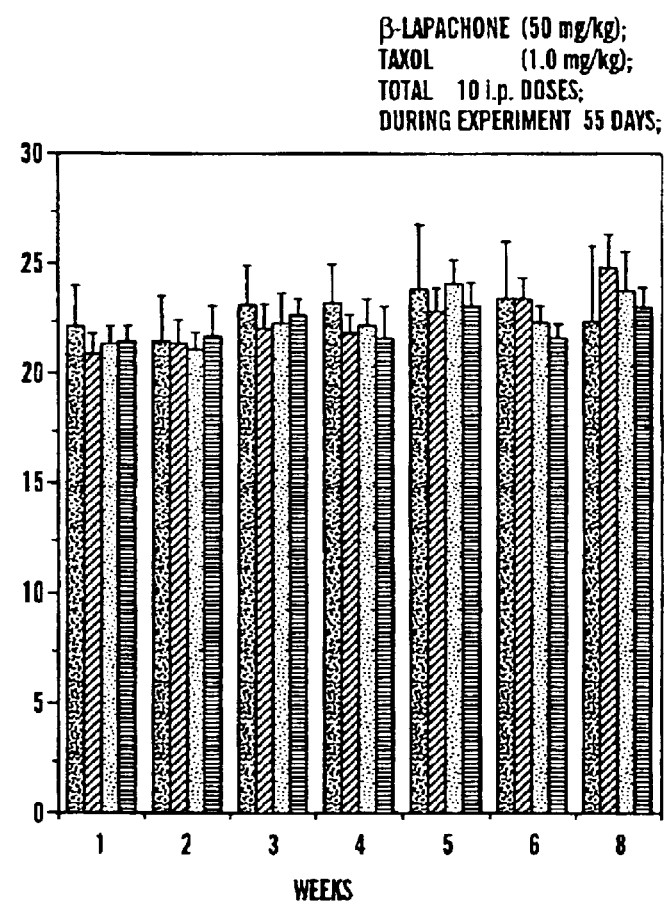

All treatments were started one week after tumor inoculation. Mice were treated for 10 cycles in total, and were sacrificed for tumor counting on day 62. The results of this experiment are set forth in FIGS. 2A and 2B. As with experiment 1, the combination of β-lapachone and TAXOL® dramatically reduced the number of tumor implants compared to the untreated control group and the groups treated with each agent alone. No toxicity was observed.

Figure 3:
FIG. 3 is a photograph of the control group showing hundreds of tumor nodules some of which have fused together to form large tumor masses (e.g., arrow 2).
Figure 4:
FIG. 4 is a photograph of the β-lapachone treated group showing several tumor nodules (e.g., arrow 2).
Figure 5:
FIG. 5 is a photograph of the paclitaxel treated group showing several tumor nodules (e.g., arrow 2).

FIGS. 3–6 visually represent the results seen in each group. In FIGS. 3–5 the peritoneal lining is red (color not shown) which is indicative of tumor stimulated blood vessel growth or angiogenesis.

The untreated mammals contain hundreds of tumor modules. Some of the nodules have fused together and formed large tumor masses (FIG. 3).

Treatment with either β-lapachone (FIG. 4) or TAXOL® (FIG. 5) resulted in a lessening of the tumors. However, the flesh in both areas was still red, signifying that substantial angiogenesis associated with the tumors was still going on. Several tumor nodules were still present in both groups treated with single therapeutic segments.

Figure 6:
FIG. 6 is a photograph of the combination treated group. No tumor nodules are visible. It is also important to note the color of the peritoneal lining. Unlike the lining seen in FIGS. 3–5, the color of the lining in the combination group is not bright red but more like that seen in healthy mice. This provides an indication that tumor growth and tumor induced angiogenesis was not occurring.

In the group receiving combination therapy, the color of the flesh is no longer bright red, but similar to that seen in healthy mice (FIG. 6). This indicates that the tumor induced angiogenesis seen in the single treatment groups is substantially inhibited or not occurring. One or two small nodules were visually observed, but are not visible in the photograph.

Experiment 3

Potent inhibition of prostate tumor growth in vivo by β-lapachone and taxol. Male SCID (ICR) mice were inoculated with androgen-independent human prostate cancer cells (DU145; 8×10$^6$ s.c.). Administration of drugs was initiated when tumor nodules reached ~0.5 cm in diameter. Four mice per group were used in this experiment. The control group (FIG. 7A) was treated with vehicle alone. The β-lapachone alone group was treated with 50 mg/kg i.p., and the taxol alone group was treated with 1 mg/kg i.p., followed 24 h later by i.p. injection of vehicle. In the combination group (FIG. 7B), mice were treated with β-lapachone alone, followed 24 h later by taxol at 1 mg/kg. There was a 1-day break between each cycle. Mice were treated for a total of six cycles. Pictures were taken 3 weeks after six cycles of treatment.

Figure 7B:
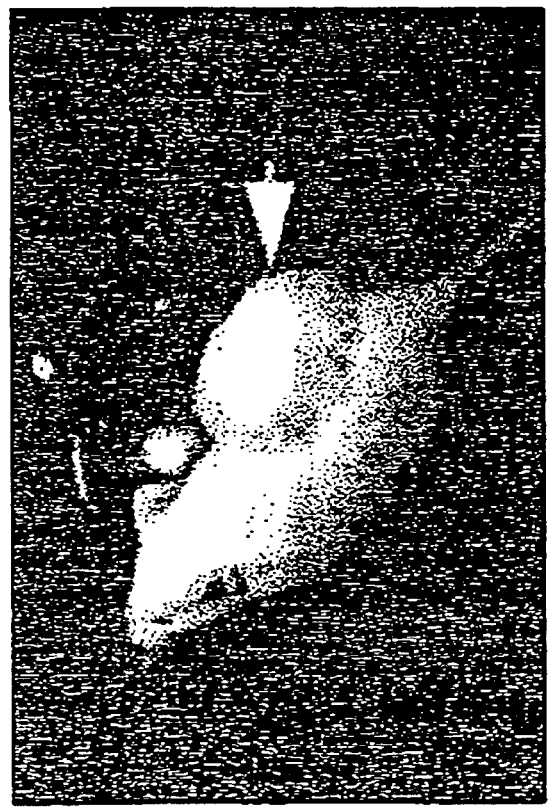
FIGS. 7A and 7B are photographs showing combination treatment on a prostate tumor.
Figure 7A:

In preliminary experiment with four mice per group, andogen-independent DU145 prostate cancer cells were xenografted into immunocompromised mice (FIG. 7A). Again, to increase stringency and unlike most antitumor experiments, treatment was delayed until the tumors reached ~0.5 cm in diameter. Either β-lapachone or taxol alone showed moderate inhibitions of tumor growth (data not shown). β-Lapachone plus taxol showed dramatic antitumor activity (FIG. 7B). Furthermore, tumors in the treated mice did not grow back as of the follow-up 6 weeks after treatment.

Experiment 4

Cell Cultures. All cell lines used in this study were obtained from the American Type Culture Collection unless specified otherwise. Cells were maintained at 37° C. in 5% $CO_2$ in complete humidity. Human breast cancer cell lines MCF-7, 21 MT, 21 PT, and 21 NT (kindly provided by R. Sager, Dana-Farber Cancer Institute) were cultured in MEM-α (Liffe Technologies, Grand Island, N.Y.), supplemented with 10% (vol/vol) FCS, 2 mM L-glutamine, and 1 mg/ml insulin. Human ovary carcinoma cell lines AD2780s and AD2780DDP, a generous gift from K. J. Scanlon (City of Hope Medical Center, Duarte, Calif.); human colon adenocarcinoma cell lines SW1116, HT-29, and DLD; human lung carcinoma cell line G480; human melanoma cell line Skmel-28, kindly provided by G. Dranoff, (Dana-Farber Cancer Institute); and human prostate tumor cell lines PC-3, DU145, and LNCaP were cultured in DMEM (Life Technologies) supplemented with 10% (vol/vol) FCS and 2 mM L-glutamine. Human pancreatic cancer cell line ASPC-1 was cultured in RPMI medium 1640 supplemented with 20% (vol/vol) FCS.

Colone Formation Assay. Exponentially growing cells were seeded at 1,000 cells per well in six-well plates and allowed to attach for 48 h. Drugs were added directly to dishes in less that 5 μl of concentrated solution (corresponding to a final DMSO concentration of less than 0.1%). Control plates received the same volume of DMSO alone. After 1–4 h, cells were rinsed, and fresh medium was added. Cultures were observed daily for 10–20 days and then were fixed and stained with modified Wright-Giemsa stain (Sigma). Colonies of greater than 30 cells were scored as survivors.

Cell Death Assay. Cell death was determined by the MTT Thiazolyl blue) assay or by trypan blue exclusion as indicated. Briefly, cells were plated in a 96-well plate at 10,000 cells per well, cultured for 48 h in complete growth medium, then treated with β-lapachone for 4 h, and cultured with drug-free medium for 24 h. MTT solution was added to the culture medium, and after 2 h. optical density was read with an ELISA reader. For the trypan blue exclusion assay, cells were cultured and treated in the same way. They were harvested, and trypan blue dye solution was added to the cell suspension. Total cell counts and viable cell numbers were determined with a hemocytometer.

Apoptosis Assays. Apoptosis was determined by three independent assays. One determined the sub-$G_1$ fraction of propidium iodide-stained nuclei as described [Li, Y.-Z, et al. *Mol. Med.* 5:232–239 (1999); Li, C. J., et al., *Science* 268:429–431 (1995); Li, C. J., et al., *Cancer Res.* 55:3712–3715 (1995). The annexin assay measured the membrane changes determined by the externalization of phosphatidylerine (Fadok, V. A., et al., *J. Immunol.* 148:2207–2216 (1992). The third assay, analysis of DNA laddering, was carried out as described by Li, Y.-Z, supra.

Synergistic induction of cell death by P-lapachone and taxol. Colony formation was carried out as described above. In a typical experiment, control DU145 cells in well 1 were treated with solvent on days 1 and 2. Cells in well 2 were treated with β-lapachone at 4 μM on day 1 for 4 h, incubated in drug-free medium for 20 H, and then treated with solvent control on day 2. Taxol-along well 3 was treated with solvent control for 4 h on day 1 and with taxol at 0.02 μM for 4 h on day 2. Cells in well 4 were treated with β-lapachone on day 1 and with taxol on day 2. In well 5, cells were treated with taxol on day 1 and with β-lapachone on day 2. In well 6, cells were treated with β-lapachone and taxol on day 2.

Synergism of the Drug Combination. Colony formation of DU145 cells in the control dish (well 1) was abolished when both taxol and β-lapachone were applied. It was decreased only partly when taxol along (well 2) or β-lapachone alone (well 3) were applied. To determine whether the order of drug addition affects this observed powerful synergism of cell killing, we varied the treatment schedule. A similar synergism was observed when cells were treated with taxol and β-lapachone simultaneously (well 6) or with β-lapachone followed by taxol (well 4). Synergism was not observed if taxol was added before β-lapachone treatment (well 5). This schedule dependency was observed in all the cell lines. These results suggest that the order of artificial checkpoint imposition is important for the synergism mechanism.

Ablation of in Vitro Colonies in a Wide Spectrum of Human Carcinoma Cells by the Combination of β-lapachone and Taxol. Human carcinoma cell lines of different histotypes were used to determine cell survival in the colony formation assay (Table 2). The combination of β-lapachone and taxol dramatically reduced cell survival in a variety of human cancer cells, including ovarian, breast, prostate, melanoma, lung, and pancreatic cancer cell lines. β-Lapachone or taxol alone at the concentrations used were much less effective in decreasing cancer cell colony formation. This decreased cell survival was achieved by induction of cell death as determined by the MTT (Thiazolyl blue) and trypan blue assays. Cell death was by apoptosis as determined by DNA laddering formation and by annexin staining (data not shown). Taxol was at least 10-fold more potent in the presence of β-lapachone, as measured at $IC_{50}$ (data not shown).

TABLE 2

Inhibition of cancer cell survival by β-lapachone and taxol

| Cell line | Tissue origins | β-Lapachone | Taxol | β-Lapachone + taxol |
|---|---|---|---|---|
| A2780DDP | Ovary | 77 (1.1) | 39 (0.8) | 0 |
| MCF-7 | Breast | 46 (1.4) | 45 (0.3) | 0 |
| 21MT | Breast | 56 (5.0) | 63 (7.0) | 0 |
| Skmel-28 | Melanoma | 56 (1.4) | 44 (5.1) | 0 |
| HT-29 | Colon | 42 (1.4) | 64 (2.5) | 0 |
| ASPC-1 | Pancreas | 45 (1.9) | 71 (0.8) | 0 |
| G480 | Lung | 32 (0.3) | 39 (2.6) | 2 (0.1) |
| DU145 | Prostate | 50 (2.2) | 30 (0.9) | 0 |

Cells were treated for 4 h with β-lapachone and/or taxol at the following concentrations: A2780DDP, β-lapachone at 2 μM and/or taxol at 0.2 μM; MCF-7 and 21-MT, β-lapachone at 4 μM and/or taxol at 0.1 μM; HT-29, β-lapachone at 4 μM; G480, β-lapachone at 4 μM and/or taxol at 0.2 μM; DU145, β-lapachone at 4 μM and/or taxol at 0.2 μM. The number of colonies in control well was taken as 100% survival. Treated wells are presented as percentage of control. Data are given as average (+SEM) from three independent experiments.

Although the foregoing invention has been described in some detail by way of illustration and example for the purposes of clarity of understanding, one skilled in the art will easily ascertain that certain changes and modifications may be practiced without departing from the spirit and scope of the appended claims.

What is claimed is:

1. A pharmaceutical composition comprising β-lapachone and a taxane derivative and a pharmaceutically acceptable carrier.

2. A kit for the treatment of a solid tumor or tumors in a mammal in need thereof comprising separate vials containing β-lapachone and a taxane derivative, with instructions for administering the β-lapachone first.

3. The kit of claim 2, wherein the taxane derivative is paclitaxel.

4. A method of treating a solid tumor or tumors in a mammal in need thereof, the method comprising:

a) administering to the mammal an effective amount of a first compound comprising β-lapachone or a derivative or analog thereof as the active ingredient; and b) administering to the mammal an effective amount of a G2/M phase drug.

5. The method of claim 4, wherein the G2/M phase drug is selected from the group consisting of microtubule targeting and topoisomerase poison drugs.

6. The method of claim 4, wherein the first compound comprises β-lapachone.

7. The method of claim 5, wherein the microtubule targeting drug is selected from the group consisting of paclitaxel, docetaxel, vincristin, vinblastin, nocodazole, epothilones and navelbine.

8. The method of claim 5, wherein the topoisomerase poison drug is selected from the group consisting of teniposide, etoposide, adriamycin, camptothecin, daunorubicin, dactinomycin, mitoxantrone, amsacrine, epirubicin and idarubicin.

9. The method of claim 4 or 5, wherein the G2/M phase drug is a taxane derivative.

10. The method of claim 4 or 5, wherein the G2/M phase drug is administered within about 24 hours after the β-lapachone or a derivative or analog thereof is administered.

11. The method of claim 4 or 5, wherein the G2/M phase drug is administered after the first compound.

12. The method of claim 9, wherein the taxane derivative is paclitaxel.

13. The method of claim 9, wherein the taxane derivative is paclitaxel and it isadministered intravenously.

14. The method of claim 9, wherein the taxane derivative is paclitaxel and it is administered intravenously after administration of the first compound.

* * * * *